United States Patent
Zanini et al.

(10) Patent No.: US 9,895,478 B2
(45) Date of Patent: Feb. 20, 2018

(54) HEMODIALYSIS ON-LINE PORT LEAK DETECTION

(71) Applicant: GAMBRO LUNDIA AB, Lund (SE)

(72) Inventors: Marco Zanini, Mirandola (IT); Marius Dinu, Medolla (IT)

(73) Assignee: Gambro Lundia AB, Lund (SE)

(*) Notice: Subject to any disclaimer, the term of this patent is extended or adjusted under 35 U.S.C. 154(b) by 320 days.

(21) Appl. No.: 14/647,869

(22) PCT Filed: Oct. 30, 2013

(86) PCT No.: PCT/IB2013/059784
§ 371 (c)(1),
(2) Date: May 28, 2015

(87) PCT Pub. No.: WO2014/083450
PCT Pub. Date: Jun. 5, 2014

(65) Prior Publication Data
US 2015/0297814 A1    Oct. 22, 2015

Related U.S. Application Data

(60) Provisional application No. 61/731,035, filed on Nov. 29, 2012.

(30) Foreign Application Priority Data

Nov. 29, 2012  (EP) ..................................... 12194716

(51) Int. Cl.
*A61M 1/16* (2006.01)
*A61M 1/34* (2006.01)
(Continued)

(52) U.S. Cl.
CPC .............. *A61M 1/14* (2013.01); *A61M 1/342* (2013.01); *A61M 1/367* (2013.01); *B01D 61/32* (2013.01);
(Continued)

(58) Field of Classification Search
CPC ........ A61M 1/14; A61M 1/16; A61M 1/1601; A61M 1/1621; A61M 1/34; A61M 1/342;
(Continued)

(56) References Cited

U.S. PATENT DOCUMENTS 7,605,710 B2 * 10/2009  Crnkovich .............. A61F 13/42
340/603
8,769,326 B2 *  7/2014  Liu ........................ G06F 1/3203
713/323
(Continued)

FOREIGN PATENT DOCUMENTS

EP      1514563       3/2005
EP      1728526      12/2006
(Continued)

OTHER PUBLICATIONS

EU Registered Community Design 001121909-0001 (1 page).
EU Registered Community Design 000552724-0001 (1 page).
EU Registered Community Design 000323522-0001 (1 page).

*Primary Examiner* — Joseph Drodge
(74) *Attorney, Agent, or Firm* — Mueting, Raasch & Gebhardt, P.A.

(57) ABSTRACT

Extracorporeal blood treatment apparatus and methods as described herein involve on-line port leak detection.

21 Claims, 4 Drawing Sheets

(51) Int. Cl.
*A61M 1/36* (2006.01)
*B01D 61/32* (2006.01)
*G08B 21/20* (2006.01)
*A61M 1/14* (2006.01)

(52) U.S. Cl.
CPC .............. *G08B 21/20* (2013.01); *A61M 1/34* (2013.01); *A61M 2205/15* (2013.01); *A61M 2205/18* (2013.01); *A61M 2205/702* (2013.01)

(58) Field of Classification Search
CPC .............. A61M 1/3424; A61M 1/3437; A61M 1/3653; A61M 1/3656; A61M 1/367; A61M 2205/18; A61M 2205/15; A61M 2205/70; A61M 2205/702; B01D 61/24; B01D 61/243; B01D 61/28; B01D 61/30; B01D 61/32; G08B 21/182; G08B 21/20
USPC ..... 73/290, 290 R, 290 B, 305, 306; 210/85, 210/86, 94, 321.6, 646; 340/603, 618, 340/619, 620, 623; 604/4.01, 5.06, 6.01, 604/6.09, 19, 65, 67, 403, 404
See application file for complete search history.

(56) References Cited

U.S. PATENT DOCUMENTS

| | | | | |
|---|---|---|---|---|
| 8,973,424 | B2 | 3/2015 | Wiktor | |
| 2002/0104890 | A1* | 8/2002 | Yoshimoto | G06K 19/0723 235/492 |
| 2002/0151804 | A1* | 10/2002 | O'Mahony | A61M 1/16 600/504 |
| 2003/0009123 | A1* | 1/2003 | Brugger | A61M 1/3626 604/4.01 |
| 2003/0126910 | A1* | 7/2003 | Burbank | A61M 1/367 73/40 |
| 2003/0128126 | A1* | 7/2003 | Burbank | A61M 1/367 340/605 |
| 2003/0136181 | A1 | 7/2003 | Balschat | |
| 2004/0129616 | A1* | 7/2004 | Mori | A61M 1/16 210/85 |
| 2005/0047959 | A1 | 3/2005 | Brandl | |
| 2010/0114001 | A1* | 5/2010 | O'Mahony | A61M 1/34 604/6.07 |
| 2011/0107251 | A1* | 5/2011 | Guaitoli | G06F 19/3418 715/772 |
| 2011/0239742 | A1 | 10/2011 | Mueller | |
| 2011/0315237 | A1 | 12/2011 | Jenkins | |
| 2011/0315611 | A1 | 12/2011 | Fulkerson | |
| 2013/0020237 | A1* | 1/2013 | Wilt | A61M 1/1037 210/85 |
| 2014/0319035 | A1* | 10/2014 | Burbank | A61M 1/367 210/143 |

FOREIGN PATENT DOCUMENTS

| | | |
|---|---|---|
| JP | 2011149912 | 8/2011 |
| WO | WO 03/058608 | 7/2003 |
| WO | WO 2004/096322 | 11/2004 |
| WO | WO 2008/021462 | 2/2008 |
| WO | WO 2010/045119 | 4/2010 |
| WO | WO 2010/062698 | 6/2010 |
| WO | WO 2012/025225 | 3/2012 |
| WO | WO 2012/108910 | 8/2012 |

* cited by examiner

HEMODIALYSIS ON-LINE PORT LEAK DETECTION

This application is a U.S. National Stage Application of International Application No. PCT/IB2013/059784, filed Oct. 30, 2013, which was published in English on Jun. 5, 2014 as International Patent Publication WO 2014/083450 A1, which claims the benefit under 35 U.S.C. 119(e) of U.S. Provisional Application No. 61/731,035 filed Nov. 29, 2012. International Application No. PCT/IB2013/059784 also claims priority to European Application No. 12194716.2, filed Nov. 29, 2012.

Apparatus and methods for detection of a hemodialysis on-line port leak are described herein.

BACKGROUND

Extracorporeal blood treatment involves taking the blood from a patient, treating the blood outside the patient, and returning the treated blood to the patient. Extracorporeal blood treatment (hemodialysis, hemofiltration for example) is typically used to extract undesirable matter or molecules (apheresis, plasmapheresis for example) from the patient's blood, and/or to add beneficial matter or molecules to the blood. The treatment is typically performed by sampling the patient's blood in a continuous or intermittent flow, by introducing the blood into a primary chamber of a filter that is defined, at least in part, by a semi-permeable membrane. The semi permeable membrane may selectively allow the unwanted matter contained in the blood pass through the membrane, from the primary chamber to the secondary chamber, and may selectively allow the beneficial matter contained in the liquid going into the secondary chamber pass through the membrane to the blood going into the primary chamber, according to the type of treatment.

Extracorporeal blood treatment is used with patients incapable of effectively eliminating matter from their blood. One example is a patient who is suffering from temporary or permanent kidney and/or liver failure. These and other patients may undergo extracorporeal blood treatment to add to or to eliminate matter from their blood, to maintain an acid-base balance, to eliminate excess body fluids, etc.

In the case of the aforementioned treatments of blood and methods of removing a blood component, the source of fluid is formed by the vascular circuit of the patient/donor, and the fluid is the blood of the patient/donor, which blood, pumped from an artery, is caused to circulate in a blood treatment apparatus (hemodialyzer, hemofilter, plasma filter, centrifuge, etc.) and, once freed of its impurities or having a fraction of one of its components reduced, is re-injected into a vein of the patient/donor.

A number of liquid supply and return lines connect with the blood treatment apparatus. These connection points can be a source of liquid leaks. Thus it is desired to provide for detection of liquid leaks at these connection points on the blood treatment apparatus.

SUMMARY

This disclosure relates to apparatus and methods for detection of a hemodialysis on-line port leak.

In one or more embodiments, an apparatus configured to remove one or more substances from blood includes: a blood pump configured to move blood through a blood circuit; an on-line port extending away from a housing of the apparatus and a liquid line coupled to the on-line port and in fluid communication with the blood circuit; a leak detector fixed to and extending from the housing of the apparatus, the leak detector comprising a collector defining a containment volume and a liquid sensor at least partially disposed within the containment volume, wherein the liquid sensor is configured to sense a liquid in the containment volume; and a control unit operably connected to the liquid sensor, wherein the control unit is configured to receive a signal from the liquid sensor where the signal is indicative of a presence of liquid in the containment volume, and determine that the liquid is leaking from the on-line port based on the signal received from the liquid sensor.

In one or more embodiments of the apparatus configured to remove one or more substances from blood as described herein, the control unit provides an alarm signal to a user interface when it is determined that liquid is leaking from the on-line port.

In one or more embodiments of the apparatus configured to remove one or more substances from blood as described herein, the control unit alters a flow rate of the blood pump when it is determined that liquid is leaking from the on-line port.

In one or more embodiments of the apparatus configured to remove one or more substances from blood as described herein, the liquid sensor is completely disposed within the containment volume.

In one or more embodiments of the apparatus configured to remove one or more substances from blood as described herein, the liquid sensor extends into the containment volume.

In one or more embodiments of the apparatus configured to remove one or more substances from blood as described herein, the collector extends further away from the housing of the apparatus than the on-line port.

In one or more embodiments of the apparatus configured to remove one or more substances from blood as described herein, the leak detector is adjacent and below the on-line port.

In one or more embodiments of the apparatus configured to remove one or more substances from blood as described herein, the signal is indicative of a presence of liquid in the containment volume when at least 25% of the containment volume is filled with liquid.

In one or more embodiments of the apparatus configured to remove one or more substances from blood as described herein, the containment volume is in a range from 10 to 30 cc.

In one or more embodiments of the apparatus configured to remove one or more substances from blood as described herein, the leak detector is configured to collect only liquid from the on-line port.

In a second aspect, one or more embodiments of a method of detecting an on-line port leak in the apparatus that includes a blood pump configured to move blood through a blood circuit; an on-line port extending away from a housing of the apparatus and a liquid line coupled to the on-line port and in fluid communication with the blood circuit; a leak detector fixed to and extending from the housing of the apparatus, the leak detector comprising a collector defining a containment volume and a liquid sensor at least partially disposed within the containment volume, wherein the liquid sensor is configured to sense a liquid in the containment volume; and a control unit operably connected to the liquid sensor, wherein the control unit is configured to receive a signal from the liquid sensor where the signal is indicative of a presence of liquid in the containment volume, and determine that the liquid is leaking from the on-line port based on the signal received from the liquid sensor. The one or more embodiments of the method as described herein may include: collecting liquid from an on-line port liquid leak in the containment volume; sensing liquid presence in the containment volume; providing a signal that is indicative of a presence of liquid in the containment volume when the sensed liquid level reaches a predetermined level in the containment volume; and determining that the liquid is leaking from the on-line port based on the signal received from the liquid sensor.

In one or more embodiments of the method of detecting an on-line port leak in the in an extracorporeal blood treatment apparatus as described herein, the providing step includes providing an alarm signal to a user interface when it is determined that liquid is leaking form the on-line port.

In one or more embodiments of the method of detecting an on-line port leak in the in an extracorporeal blood treatment apparatus as described herein, the providing step includes altering a flow rate of the blood pump when it is determined that liquid is leaking form the on-line port.

In a third aspect, one or more embodiments of a use of the extracorporeal blood treatment apparatus described herein to detect an on-line port liquid leak, is described The above summary is not intended to describe each embodiment or every implementation of the extracorporeal blood treatment apparatus and methods described herein. Rather, a more complete understanding of the disclosure will before apparent and appreciated by reference to the following Description of Illustrative Embodiments and claims in view of the accompanying figures of the drawings.

BRIEF DESCRIPTION OF THE VIEWS OF THE DRAWING

The disclosure may be more completely understood in consideration of the following detailed description of various embodiments of the disclosure in connection with the accompanying drawings, in which.

DESCRIPTION OF ILLUSTRATIVE EMBODIMENTS

Figure 1:
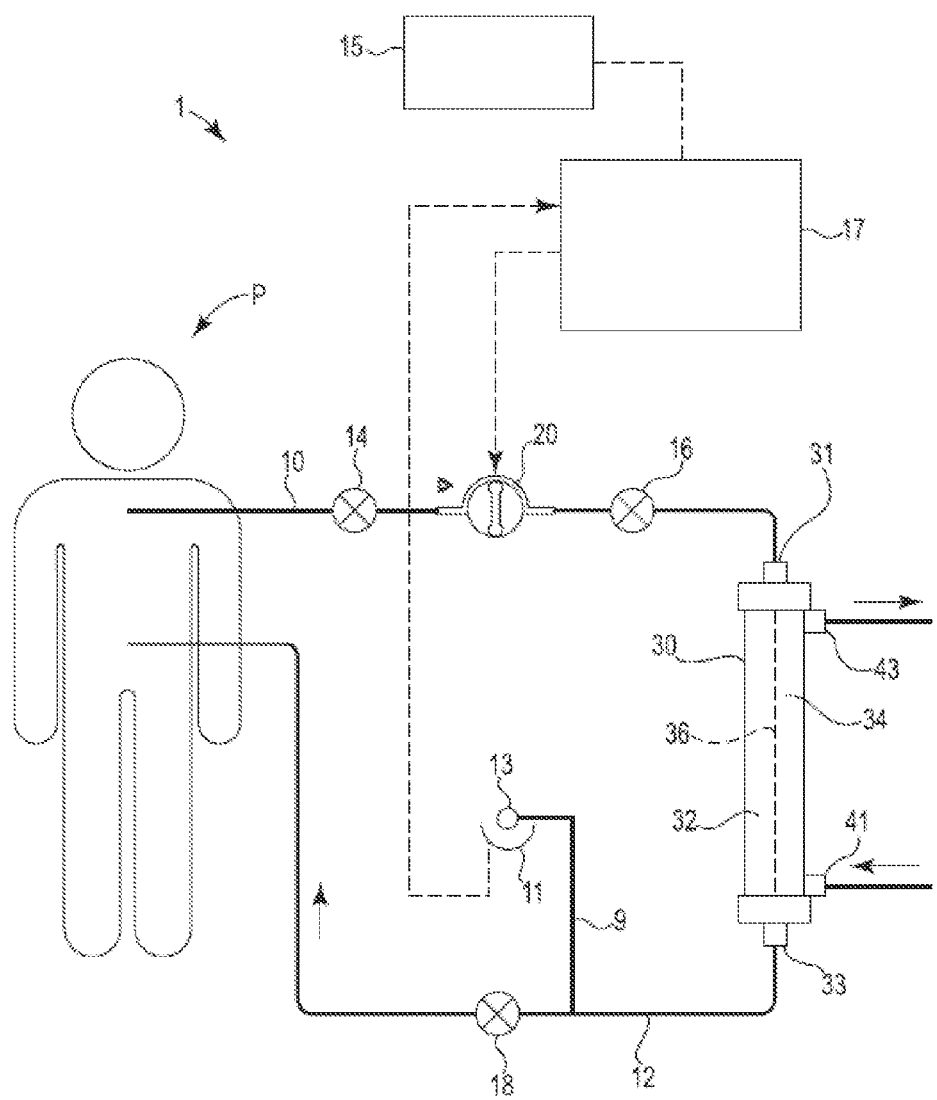
FIG. 1 depicts a schematic diagram of an illustrative embodiment of an hemodialysis apparatus described herein.

In the following detailed description, reference is made to the accompanying drawings that form a part hereof, and in which are shown by way of illustration several specific embodiments. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

In the following description of illustrative embodiments, reference is made to the accompanying figures of the drawing which form a part hereof, and in which are shown, by way of illustration, specific embodiments. It is to be understood that other embodiments may be utilized and structural changes may be made without departing from the scope of the present invention.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

As used in this specification and the appended claims, the singular forms "a," "an," and "the" encompass embodiments having plural referents, unless the content clearly dictates otherwise. As used in this specification and the appended claims, the term "or" is generally employed in its sense including "and/or" unless the content clearly dictates otherwise.

Spatially related terms, including but not limited to, "lower," "upper," "beneath," "below," "above," and "on top," if used herein, are utilized for ease of description to describe spatial relationships of an element(s) to another. Such spatially related terms encompass different orientations of the device in use or operation in addition to the particular orientations depicted in the figures and described herein. For example, if an object depicted in the figures is turned over or flipped over, portions previously described as below or beneath other elements would then be above those other elements.

As used herein, when an element, component or layer for example is described as forming a "coincident interface" with, or being "on" "connected to," "coupled with" or "in contact with" another element, component or layer, it can be directly on, directly connected to, directly coupled with, in direct contact with, or intervening elements, components or layers may be on, connected, coupled or in contact with the particular element, component or layer, for example. When an element, component or layer for example is referred to as being "directly on," "directly connected to," "directly coupled with," or "directly in contact with" another element, there are no intervening elements, components or layers for example.

As used herein, "have", "having", "include", "including", "comprise", "comprising" or the like are used in their open ended sense, and generally mean "including, but not limited to." It will be understood that the terms "consisting of" and "consisting essentially of" are subsumed in the term "comprising," and the like.

This disclosure relates to apparatus and methods for detection of a hemodialysis on-line port leak, among other aspects. The hemodialysis or extracorporeal blood treatment apparatus includes a leak detector configured to receive liquid leaking from an on-line port of the hemodialysis or extracorporeal blood treatment apparatus and provide a signal to a control unit indicating a leak at the on-line port. The control unit can provide an alarm signal to a user interface or alter the operation of the extracorporeal blood treatment apparatus. The leak detector includes a collector with a specified containment volume that can be configured to collect liquid from a single on-line port and provide a leak signal at any specified leak volume. While the present disclosure is not so limited, an appreciation of various aspects of the disclosure will be gained through a discussion of the examples provided below.

In the illustrative embodiment depicted in FIG. 1, the extracorporeal blood treatment apparatus 1 includes a blood circuit having an arterial line 10 that delivers blood from a patient P to a blood compartment 32 of a primary filter 30. The blood in the blood circuit is returned to the patient P through a venous return line 12. The blood compartment 32 of the primary filter 30 is separated from an dialysate compartment 34 in the primary filter 30 by a semipermeable membrane 36. Although the primary filter 30 is depicted simplistically as having only one blood compartment 32 and one dialysate compartment 34, the primary filter 30 depicted in FIG. 1 should not be construed to limit the apparatus and methods described herein to such a simple embodiment. For example, the blood compartments or the dialysate compartments in the primary filters of extracorporeal blood treatment apparatus described herein may be, e.g., defined by a plurality of hollow fibers constructed of a semipermeable material as is known in the art. It is understood that the extracorporeal blood treatment apparatus is not limited to the dialysis treatment apparatus illustrated by can be applied to any extracorporeal blood treatment apparatus, as desired.

In the illustrated embodiment, as the patient's blood moves through the blood circuit and the blood compartment 32 along the membrane 36, undesirable matter or molecules (apheresis, plasmapheresis for example) in the blood are transported through the membrane 36 and into the dialysate in the dialysate compartment 34 (such that the dialysate is "loaded" with the undesirable matter or molecules from the blood).

The blood circuit of the apparatus 1 of FIG. 1 also includes a blood pump 20 that can be configured to move blood through the blood compartment 32 of the primary filter 30, with the blood entering the blood compartment 32 through an inlet 31 to which the arterial line 10 is connected, for example. Blood in the blood circuit leaves the blood compartment 32 through an outlet 33 to which the venous line 12 is connected. Although depicted as a roller pump, the blood pump 20 may be of any suitable design (e.g., a roller pump, piston pump, diaphragm pump, etc.) or other flow control mechanism (e.g., valves, clamps, etc.), etc.

The blood circuit depicted in FIG. 1 also includes one or more pressure sensors configured to measure pressure at various locations in the blood circuit. In the depicted embodiment, the blood circuit includes an access pressure sensor 14 located between the patient P and the blood pump 20. The access pressure sensor 14 may be used to monitor pressure in the arterial line 10 downstream of the patient P and upstream of the blood pump 20.

The blood circuit of FIG. 1 includes a filter pressure sensor 16 located downstream from the blood pump 20 and upstream of the blood chamber 32 of the primary filter 30. The filter pressure sensor 16 is used to monitor pressure in the arterial line 10.

A third pressure sensor in the form of a return pressure sensor 18 can be located along the venous return line 12 downstream of the blood compartment 32 of the primary filter 30 and upstream of the patient P. The return pressure sensor 18 monitors pressure in the blood circuit after the blood has passed through the blood compartment 32 and before it is returned to the patient P.

The exemplary extracorporeal blood treatment apparatus 1 depicted in FIG. 1 also includes an dialysate circuit configured to move dialysate through the dialysate compartment 34 of the primary filter 30. In the dialysate circuit, the dialysate enters the dialysate compartment 34 of the primary filter through an inlet 41 and leaves the dialysate solution loading compartment 34 through an outlet 43.

The illustrated on-line port 13 is in fluid connection with the blood circuit venous return line 12 via an infusion line 9. It is understood that the on-line port 13 is in fluid connection with the blood circuit at any useful location along the blood circuit. An infusion supply and infusion pump is not illustrated but can be located upstream of the on-line port 13. The on-line port 13 can provide liquid to the blood circuit via an infusion line 9. For example, the on-line port 13 can provide liquid to restore a liquid volume that was removed from the blood line through the primary filter during the dialysis process. Exact metering of this infusion liquid through the infusion line 9 is desired and a disruption in this mass balance can cause problems with the blood circuit. Thus leak detection at the on-line port 13 connection with the infusion line 9 is useful to ensuring the integrity of the mass balance of the infusion liquid into the blood circuit.

A leak detector 11 is associated with the on-line port 13 connection with the infusion line 9. A control unit 17 is operably connected to the leak detector 11, a user interface 15 and control elements (the blood pump 20, for example) of the blood circuit and control elements of the on-line port 13 infusion supply. The control unit 17 is configured to monitor the leak detector 11 signal and operate at least one of the control elements (the blood pump 20, for example) of the blood circuit or one of the control elements of the on-line port 13 infusion supply or supply an alarm signal to a user interface, based on the monitored leak detector 11 signal.

The liquid sensor described herein can operate via number of different principles. In one or more embodiments the liquid sensor can operate via ultrasonic, capacitive or optical principles. One exemplary optical liquid sensor is commercially available under the trade designation LLE Series Liquid Level Sensor from Honeywell International, Morristown, N.J. The LLE Series Liquid Level Sensor employs an infra-red LED and phototransistor positioned at the base of the sensor's tip. When the tip is air, infra-red light reflects internally round the tip to the phototransistor providing optical coupling between the two. When the sensor's tip is immersed in liquid, the infra-red light escapes from the tip causing a change in the amount of light at the phototransistor which makes the output change state. One exemplary capacitive liquid level switch is commercially available under the trade designation CLW Series Capacitive Point Liquid Level Sensor from First Sensor AG., Munich, Germany.

Various components of the extracorporeal blood treatment apparatus described herein that may be operably connected to the control unit 17. The leak detector 11 and the blood pump 20 of the blood circuit are operably connected to the control unit 17. In addition, other control elements of the blood circuit can also operably connected to the control unit 17. These other control elements include flow control devices such as valves, clamps and pumps for example, and pressure sensors such as the return pressure sensor 18 and access pressure sensor 14 for example.

The control unit 17 may be provided in any suitable form and may, for example, include memory and a controller. The controller may, for example, be in the form of one or more microprocessors, Application Specific Integrated Circuit (ASIC) state machines, etc. The control unit 17 may include one or more of any suitable input devices configured to allow a user to operate the apparatus (e.g., keyboards, touchscreens, mice, trackballs, etc.), as well as display devices or user interfaces 15 configured to convey information to a user (e.g., monitors (which may or may not be touchscreens), indicator lights, etc.).

In one or more embodiments the control unit 17 is configured to take action once the leak detector 11 indicates a leak is present at the on-line port 13. This action can include at least one of, providing an alarm indication, or altering a flow rate of the blood pump 20 or the infusion pump.

Figure 2:
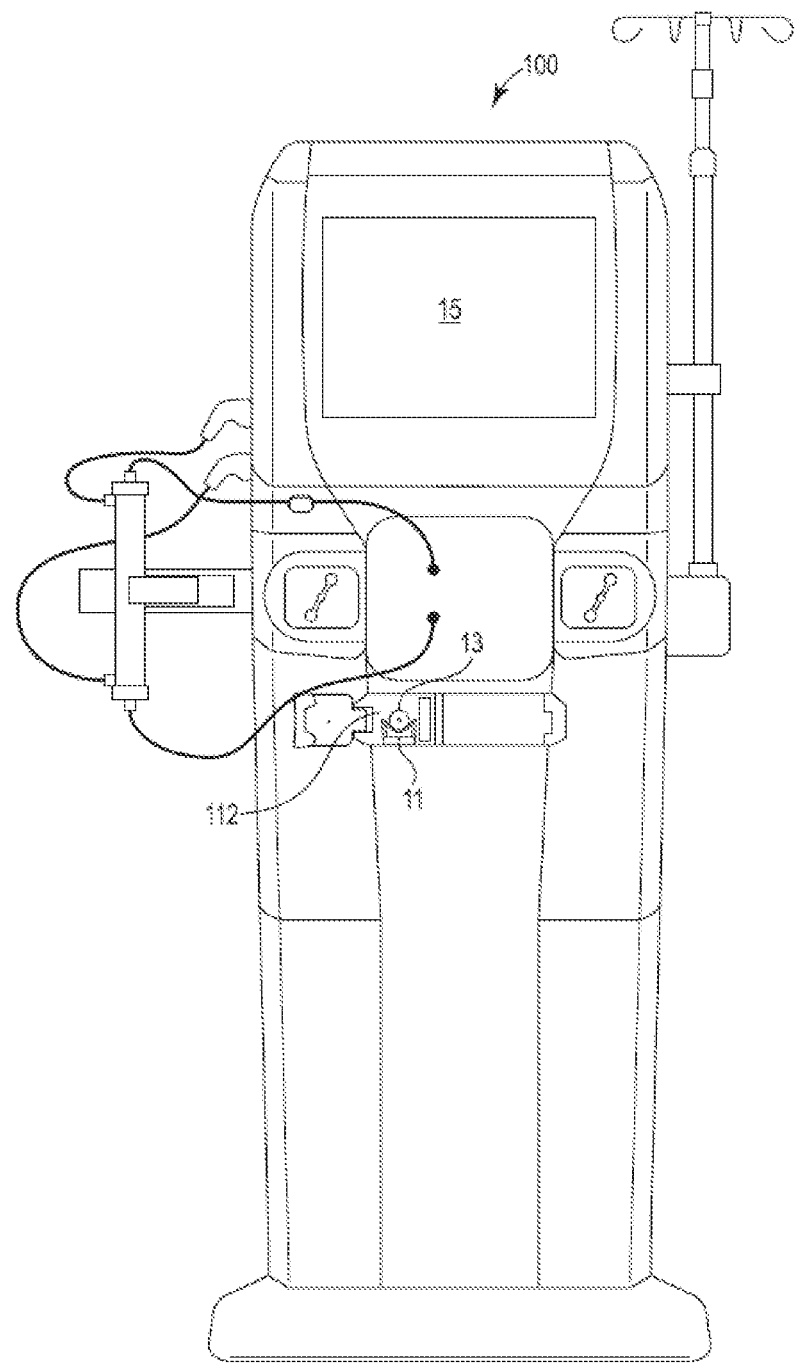
FIG. 2 depicts an illustrative hemodialysis therapy unit.
Figure 3:
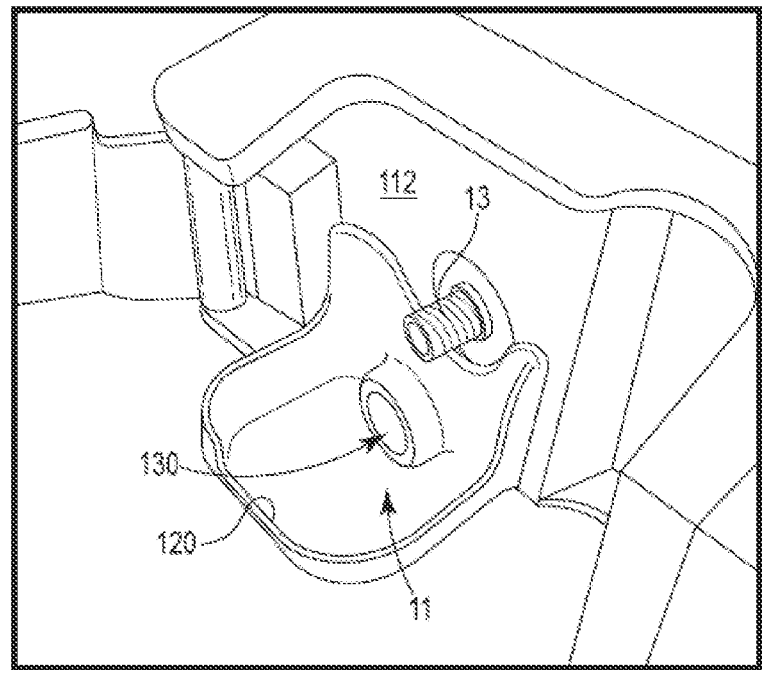
FIG. 3 depicts an perspective view of an illustrative placement of a leak detector article on the dialysis therapy unit shown in FIG. 2.
Figure 4:
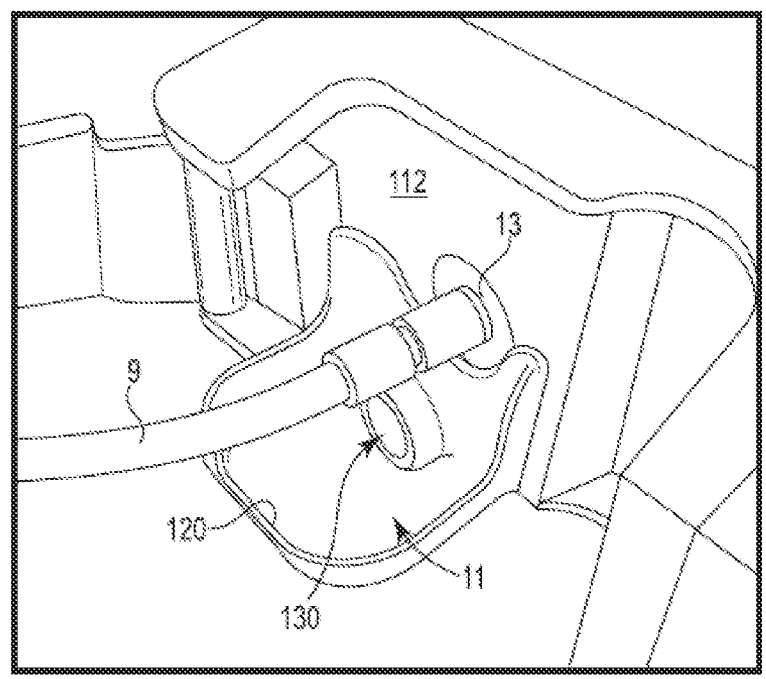
FIG. 4 depicts another perspective view of an illustrative leak detector article on the dialysis therapy unit shown in FIG. 2 with a liquid line connected to an on-line port
Figure 5:
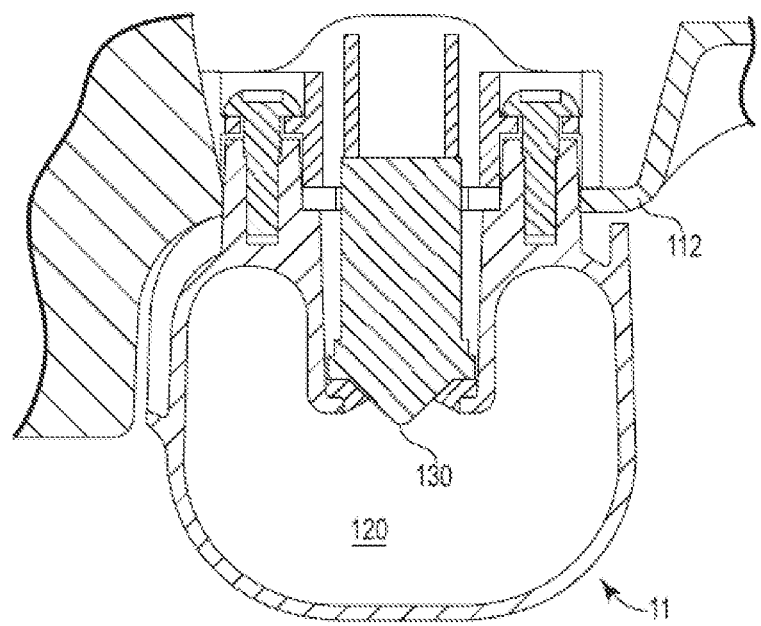
FIG. 5 depicts a schematic diagram top view of an illustrative leak detector article.
Figure 6:
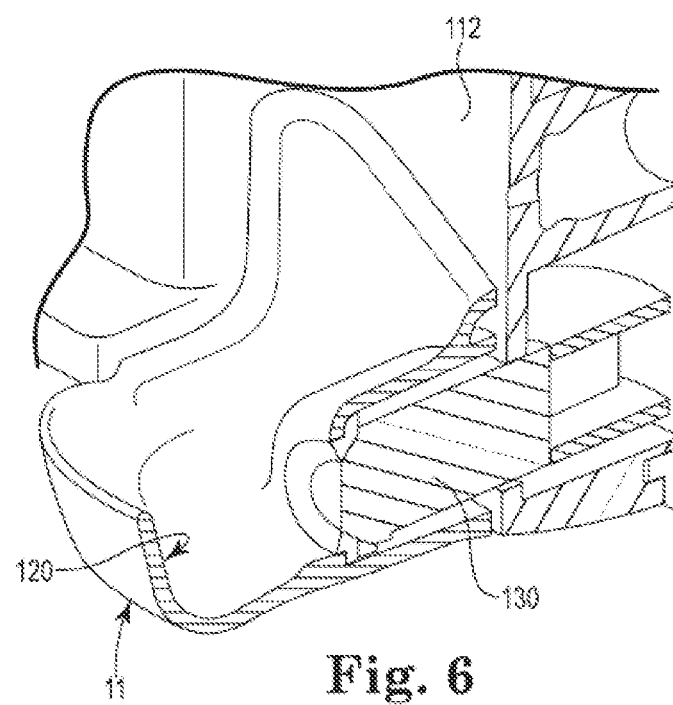
FIG. 6 depicts a schematic diagram cross-sectional side view of an illustrative leak detector article.

FIG. 2 depicts an illustrative placement of an on-line port 13 leak detector 11 on an exemplary hemodialysis therapy unit 100. FIG. 3 depicts an perspective view of the on-line port 13 leak detector 11 shown in FIG. 2. FIG. 4 depicts another perspective view of the illustrative leak detector 11 on the dialysis therapy unit shown in FIG. 2 with a liquid line 9 connected to an on-line port 13. FIG. 5 depicts a schematic diagram top view of an illustrative leak detector 11. FIG. 6 depicts a schematic diagram cross-sectional side view of an illustrative leak detector 11.

The leak detector 11 can be fixed to and extend from the housing 112 of the extracorporeal blood treatment apparatus 100. The leak detector 11 can include a collector 120 defining a containment volume and a liquid sensor 130 at least partially disposed within the containment volume. The liquid sensor 130 is configured to sense a liquid in the containment volume. The control unit 17 is configured to receive a signal from the leak detector 11 or liquid sensor 130 where the signal is indicative of a presence of liquid in the containment volume and determine that the liquid is leaking from the on-line port 13 based on the signal received from the liquid sensor 130.

In one or more embodiments, the control unit 17 provides an alarm signal to a user interface 15 when it is determined that liquid is leaking from the on-line port 13. The control unit 17 can control or alter the extracorporeal blood treatment apparatus 100 or one or more of the control elements of the extracorporeal blood treatment apparatus 100 when it is determined that liquid is leaking from the on-line port 13, such as altering the blood flow rate of the blood pump 20 for example.

In one or more embodiments, the liquid sensor 130 is completely disposed within the containment volume of the collector 120. The collector 120 can define an open tray receptacle defining an opening for the liquid sensor 130. In many embodiments the liquid sensor 130 extends into the containment volume. In many embodiments, the collector 120 extends further away from the housing 112 of the extracorporeal blood treatment apparatus 100 than the on-line port 13. In many embodiments, the leak detector 11 is adjacent and below the on-line port 13 and is arranged and configured to catch a leak from the on-line port 13 and liquid line 9 connection via gravity.

In one or more embodiments, the signal from the liquid sensor 130 is indicative of a presence of liquid in the containment volume when at least 25% of the containment volume is filled with liquid. The containment volume can be any useful volume amount. In some embodiments the containment volume is in a range from 10 cc to 30 cc.

In one or more embodiments, the leak detector 11 is configured to collect only liquid from the on-line port 13 or from the on-line port 13 and liquid line 9 connection.

In one or more embodiments of a method of detecting an on-line port leak in a extracorporeal blood treatment apparatus includes: collecting liquid from an on-line port liquid leak in the containment volume; sensing liquid presence in the containment volume; providing a signal that is indicative of a presence of liquid in the containment volume when the sensed liquid level reaches a predetermined level in the containment volume; and determining that the liquid is leaking from the on-line port based on the signal received from the liquid sensor. In one or more embodiments the providing step includes providing an alarm signal to a user interface when it is determined that liquid is leaking form the on-line port. In one or more embodiments the providing step includes controlling or altering the apparatus when it is determined that liquid is leaking form the on-line port.

The complete disclosure of the patents, patent documents, and publications identified herein are incorporated by reference in their entirety as if each were individually incorporated.

Thus, embodiments of HEMODIALYSIS ON-LINE PORT LEAK DETECTION are disclosed. One skilled in the art will appreciate that the compositions described herein can be practiced with embodiments other than those disclosed. The disclosed embodiments are presented for purposes of illustration and not limitation. Accordingly, the invention is to be limited only by the claims provided below and equivalents thereof.

The invention claimed is:

1. An apparatus comprising:
    a blood pump configured to move blood through a blood circuit;
    an on-line port extending away from a housing of the apparatus and a liquid line coupled to the on-line port and in fluid communication with the blood circuit;
    a leak detector fixed to and extending from the housing of the apparatus, the leak detector comprising a collector defining a containment volume and a liquid sensor at least partially located within the containment volume, wherein the collector is located adjacent and below the on-line port and configured to collect liquid leaking from the on-line port, wherein the liquid sensor is configured to sense a liquid in the containment volume; and
    a control unit operably connected to the liquid sensor, wherein the control unit is configured to:
    receive a signal from the liquid sensor, and
    determine that the liquid is leaking from the on-line port based on the signal received from the liquid sensor.

2. An apparatus according to claim 1, wherein the control unit is configured to provide an alarm signal to a user interface when it is determined that liquid is leaking from the on-line port.

3. An apparatus according to claim 1, wherein the control unit is configured to alter a flow rate of the blood pump when it is determined that liquid is leaking from the on-line port.

4. An apparatus according to claim 1, wherein the liquid sensor is completely located within the containment volume.

5. An apparatus according to claim 1, wherein the liquid sensor extends into the containment volume.

6. An apparatus according to claim 1, wherein the collector extends further away from the housing of the apparatus than the on-line port.

7. An apparatus according to claim 1, wherein the signal issued by the sensor is indicative of a presence of liquid in the containment volume.

8. An apparatus according to claim 7, wherein the control unit is configured determine that the liquid is leaking from the on-line port when the signal indicative of a presence of liquid in the containment volume indicates that at least 25% of the containment volume is filled with liquid.

9. An apparatus according to claim 1, wherein the signal issued by the sensor is indicative of a quantity of liquid in the containment volume.

10. An apparatus according to claim 1, wherein the control unit is configured to alter one or more control elements of an extracorporeal blood treatment apparatus when it is determined that liquid is leaking from the on-line port, said one or more control elements controlling one or more of: the blood pump and an infusion line located upstream of the on-line port and fluidly connected to the online port.

11. An apparatus according to claim 10, wherein the altering one or more control elements comprises one or more of:
altering a blood flow rate set for the blood pump,
stopping the blood pump,
altering a fluid flow set for an infusion pump,
stopping an infusion pump,
stopping the blood pump and an infusion pump.

12. An apparatus according to claim 1, wherein the sensor is configured for issuing the signal, wherein the signal is indicative of a presence of liquid in the containment volume when at least 25% of the containment volume is filled with liquid.

13. An apparatus according to claim 1, wherein the containment volume is in a range from 10 to 30 cc.

14. An apparatus according to claim 1, wherein the leak detector is configured to collect only liquid coming from the on-line port.

15. An apparatus according to claim 1, wherein the collector extends further away from the housing of the apparatus than the on-line port and defines an open tray receptacle defining an opening for the liquid sensor.

16. An apparatus comprising:
a blood pump configured to move blood through a blood circuit;
an on-line port extending away from a housing of the apparatus and a liquid line coupled to the on-line port and in fluid communication with the blood circuit;
a leak detector fixed to and extending from the housing of the apparatus, the leak detector comprising a collector defining a containment volume configured to catch liquid leaking from the on-line port and a liquid sensor at least partially located within the containment volume, wherein the liquid sensor is configured to sense liquid in the containment volume, the collector extending further away from the housing of the apparatus than the on-line port and defining an open tray receptacle defining an opening for the liquid sensor, and the collector being adjacent and below the on-line port and configured to collect liquid leaking from the on-line port; and
a control unit operably connected to the liquid sensor, wherein the control unit is configured to:
receive a signal from the liquid sensor, and
determine that the liquid is leaking from the on-line port based on the signal received from the liquid sensor.

17. An apparatus comprising:
a blood pump configured to move blood through a blood circuit;
an on-line port extending away from a housing of the apparatus and a liquid line coupled to the on-line port and in fluid communication with the blood circuit;
a leak detector fixed to and extending from the housing of the apparatus, the leak detector comprising a collector defining a containment volume configured to catch only liquid leaking from the on-line port and a liquid sensor at least partially located within the containment volume, wherein the liquid sensor is configured to sense liquid in the containment volume; and
a control unit operably connected to the liquid sensor, wherein the control unit is configured to:
receive a signal from the liquid sensor, and
determine that the liquid is leaking from the on-line port based on the signal received from the liquid sensor.

18. An apparatus comprising:
a blood pump configured to move blood through a blood circuit;
an on-line port extending away from a housing of the apparatus and a liquid line coupled to the on-line port and in fluid communication with the blood circuit;
a leak detector fixed to and extending from the housing of the apparatus, the leak detector comprising a collector defining a containment volume and a liquid sensor at least partially located within the containment volume, wherein the liquid sensor is configured to sense a liquid in the containment volume, the leak detector being configured to collect only liquid coming from the on-line port; and
a control unit operably connected to the liquid sensor, wherein the control unit is configured to:
receive a signal from the liquid sensor, and
determine that the liquid is leaking from the on-line port based on the signal received from the liquid sensor.

19. An apparatus according to claim 18, wherein the collector of the leak detector is adjacent and below the on-line port such that the collector is configured to collect liquid leaking from the on-line port.

20. An apparatus according to claim 18, wherein the collector extends further away from the housing of the apparatus than the on-line port and defines an open tray receptacle defining an opening for the liquid sensor, and wherein the leak detector is adjacent and below the on-line port.

21. An apparatus according to claim 17, wherein the collector extends further away from the housing of the apparatus than the on-line port and defines an open tray receptacle defining an opening for the liquid sensor, and wherein the leak detector is adjacent and below the on-line port.

* * * * *